(12) United States Patent
McLachlin et al.

(10) Patent No.: US 10,166,079 B2
(45) Date of Patent: Jan. 1, 2019

(54) DEPTH-ENCODED FIDUCIAL MARKER FOR INTRAOPERATIVE SURGICAL REGISTRATION

(71) Applicants: Stewart David McLachlin, Toronto (CA); Kamyar Abhari, Toronto (CA); Gal Sela, Toronto (CA); Jared Rowland Shoup, Toronto (CA); Kai Michael Hynna, Toronto (CA)

(72) Inventors: Stewart David McLachlin, Toronto (CA); Kamyar Abhari, Toronto (CA); Gal Sela, Toronto (CA); Jared Rowland Shoup, Toronto (CA); Kai Michael Hynna, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

(21) Appl. No.: 15/911,874

(22) Filed: Mar. 5, 2018

(65) Prior Publication Data

US 2018/0256264 A1    Sep. 13, 2018

(51) Int. Cl.
| | |
|---|---|
| *A61B 3/00* | (2006.01) |
| *A61B 34/20* | (2016.01) |
| *A61B 90/00* | (2016.01) |
| *A61B 34/30* | (2016.01) |

(52) U.S. Cl.
CPC ............ *A61B 34/20* (2016.02); *A61B 90/39* (2016.02); *A61B 34/30* (2016.02); *A61B 2034/2055* (2016.02); *A61B 2034/2065* (2016.02); *A61B 2090/3983* (2016.02)

(58) Field of Classification Search
CPC ................................ A61B 34/20; A61B 90/39
See application file for complete search history.

(56) References Cited

U.S. PATENT DOCUMENTS

| | | | |
|---|---|---|---|
| 2007/0287902 A1* | 12/2007 | Fuimaono | A61B 5/055 600/300 |
| 2016/0135904 A1* | 5/2016 | Daon | A61B 6/032 600/424 |
| 2017/0135602 A1* | 5/2017 | Izmirli | A61B 5/6852 |
| 2017/0358131 A1* | 12/2017 | Weiss | G06F 3/0416 |

* cited by examiner

*Primary Examiner* — Edward Park
(74) *Attorney, Agent, or Firm* — Ridout & Maybee LLP

(57) ABSTRACT

Methods and systems of performing intraoperative image registration during a medical procedure are described. A depth-encoded marker is provided to an object of interest. The marker is imageable by at least two imaging systems. The marker has asymmetry in at least a depth dimension. First and second sets of image data are obtained. Tracking data is obtained. The first image coordinate space, the second image coordinate space and the tracking coordinate space are independent from each other. Transformation mapping is performed to register the first and second sets of image data and the tracking data to each other. The first and second sets of image data are mapped to each other based on the depth-encoded marker. The first or second set of image data and the tracking data are mapped to each other based the same or different marker.

24 Claims, 12 Drawing Sheets

DEPTH-ENCODED FIDUCIAL MARKER FOR INTRAOPERATIVE SURGICAL REGISTRATION

FIELD

The present disclosure relates to methods and systems for intraoperative surgical registration. The present disclosure also relates to fiducial markers suitable for intraoperative surgical registration.

BACKGROUND

A common problem with image-guided spinal navigation is registration of the bony surface anatomy to the optical tracking system. Intraoperative three-dimensional (3D) imaging may be used to optically track the imaging system. However, a solution is needed to enable automatic registration of intraoperative image data with optical tracking data.

Further, registration is needed to transform tracking data to preoperative image data (e.g., magnetic resonance (MR) or computed tomography (CT) image data). Conventionally, this registration may be accomplished through collecting touch points (e.g., either fiducial or anatomic points) using a physical stylus. However, touch point collection is subject to user variability, and the physical stylus used for collecting the points can deform or deflect patient skin position. Another conventional approach involves detecting anatomical points, which are matched to the image set surface contour. However, this requires clean exposed bone, in the case of spinal navigation, which can be time-consuming to achieve. Further, using the conventional methods, if registration is lost, re-registration is difficult if not impossible to be completed again during surgery.

It would be useful to provide registration of intraoperative image data with optical tracking data and preoperative image data.

SUMMARY

In some examples, the present disclosure describes a method of performing intraoperative image registration during a medical procedure. A depth-encoded marker is provided to an object of interest. The marker is imageable by at least two imaging systems, and the marker has asymmetry in at least a depth dimension that is detectable by the at least two imaging systems. A first set of image data of the object of interest is obtained using a first imaging system, the first set of image data encompassing the marker, the first set of image data being in a first image coordinate space. A second set of image data of the object of interest is obtained using a second imaging system, the second set of image data encompassing the marker, the second set of image data being in a second image coordinate space. Tracking data is obtained tracking the same or different marker, using a tracking system, the tracking data being in a tracking coordinate space. The first image coordinate space, the second image coordinate space and the tracking coordinate space are independent from each other. A transformation mapping is performed to register the first set of image data, the second set of image data and the tracking data to each other. The first and second sets of image data are mapped to each other based on a determination of three-dimensional (3D) position and orientation of the marker in each of the first and second sets of image data. The first or second set of image data and the tracking data are mapped to each other based on a determination of 3D position and orientation of the same or different marker in each of the tracking data and the first or second set of image data.

In some examples, the present disclosure describes a system for performing intraoperative image registration during a medical procedure. The system includes a depth-encoded marker for an object of interest. The marker is imageable by at least two imaging systems, and the marker has asymmetry in at least a depth dimension that is detectable by the at least two imaging systems. The system also includes a tracking system for obtaining intraoperative tracking data of the same or different marker. The tracking data is in a tracking coordinate space. The system also includes a navigation system, the navigation system including a memory and a processor. The memory stores a first set of image data of the object of interest. The first set of image data encompasses the marker, and the first set of image data is in a first image coordinate space. The system also includes an imaging system for obtaining a second set of image data of the object of interest. The second set of image data encompasses the marker, and the second set of image data is in a second image coordinate space. The first image coordinate space, the second image coordinate space and the tracking coordinate space are independent from each other. The processor of the navigation system is configured to receive the tracking data and the second set of image data from the tracking system and the imaging system, respectively. The processor is also configured to perform a transformation mapping to register the first set of image data. The first and second sets of image data are mapped to each other based on a determination of three-dimensional (3D) position and orientation of the marker in each of the first and second sets of image data. The first or second set of image data and the tracking data are mapped to each other based on a determination of 3D position and orientation of the same or different marker in each of the tracking data and the first or second set of image data. The processor is also configured to store registration data in the memory based on the transformation mapping.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DESCRIPTION OF EXAMPLE EMBODIMENTS

Figure 1:
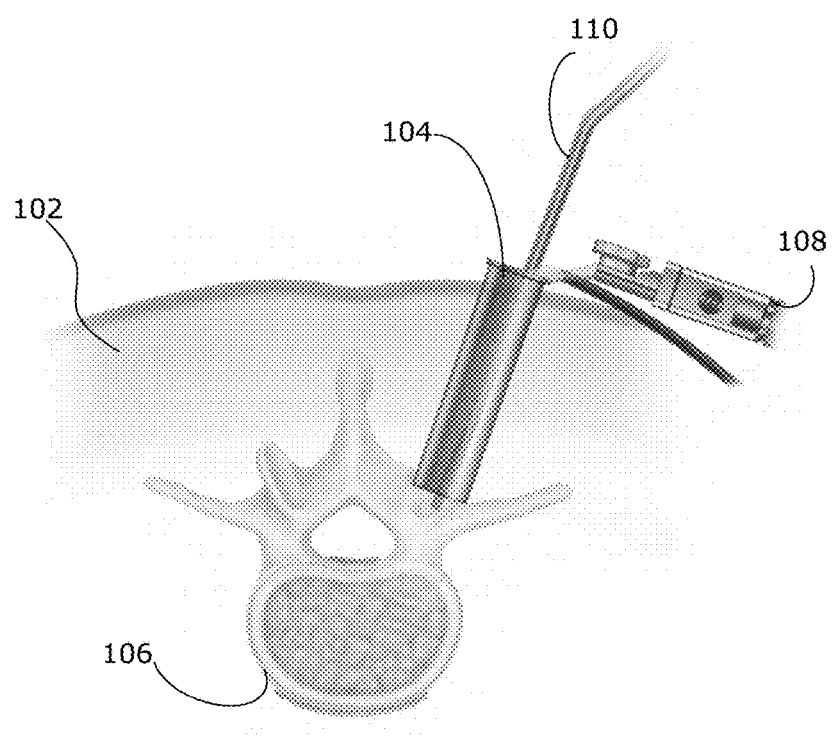
FIG. 1 illustrates the use of a retractor tube to access a patient's spine.

The systems and methods described herein may be useful for various medical procedures, including spinal procedures, neural procedures and orthopaedic procedures. The systems and methods described herein may be useful for co-registration of preoperative and intraoperative image data, together with tracking data. The present disclosure may also be useful for co-registration of two or more sets of intraoperative image data, or two or more sets of preoperative image data, together with tracking data. The teachings of the present disclosure may be applicable to other conditions or fields of medicine. It should be noted that while the present disclosure describes examples in the context of spinal surgery, the present disclosure may be applicable to other procedures that may benefit from depth-based image registration.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" or "example" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

As used herein the phrase "preoperative" refers to an action, process, method, event or step that occurs prior to the start of a medical procedure. Preoperative, as defined herein, is not limited to surgical procedures, and may refer to other types of medical procedures, such as diagnostic and therapeutic procedures. Planning a medical procedure may be considered to be preoperative.

Some embodiments of the present disclosure provide imaging devices that are insertable into a subject or patient for imaging internal tissues, and methods of use thereof. Some embodiments of the present disclosure relate to minimally invasive medical procedures that are performed via an access port or retractor tube, whereby surgery, diagnostic imaging, therapy, or other medical procedures (e.g., minimally invasive medical procedures) are performed based on access to internal tissue through the access port or retractor tube.

FIG. 1 illustrates an example minimally invasive spinal procedure in a patient 102. In FIG. 1, a retractor tube 104 is used to access a surgical site on the spine 106 of the patient 102. The retractor tube 104 may be held by a clamp 108. The retractor tube 104 may provide a passage for a medical instrument 110 to access the spine 106. For example, medical instruments such as catheters, surgical probes, or other surgical tools may be inserted within the lumen of the retractor tube 104 in order to perform surgical, diagnostic or therapeutic procedures.

Although described in the context of a spinal medical procedure, the present disclosure may also be applicable to other medical procedures including, for example, neurosurgical procedures, orthopaedic procedures, biopsy procedures or other medical procedures performed on other parts of the body, as well as medical procedures that do not use an access port or retractor tube.

Optical tracking systems, used in the medical procedure, track the position of a part of the instrument that is within line-of-sight of the optical tracking camera. Other tracking systems may be used, such as electromagnetic or mechanical based tracking systems.

Figure 2:
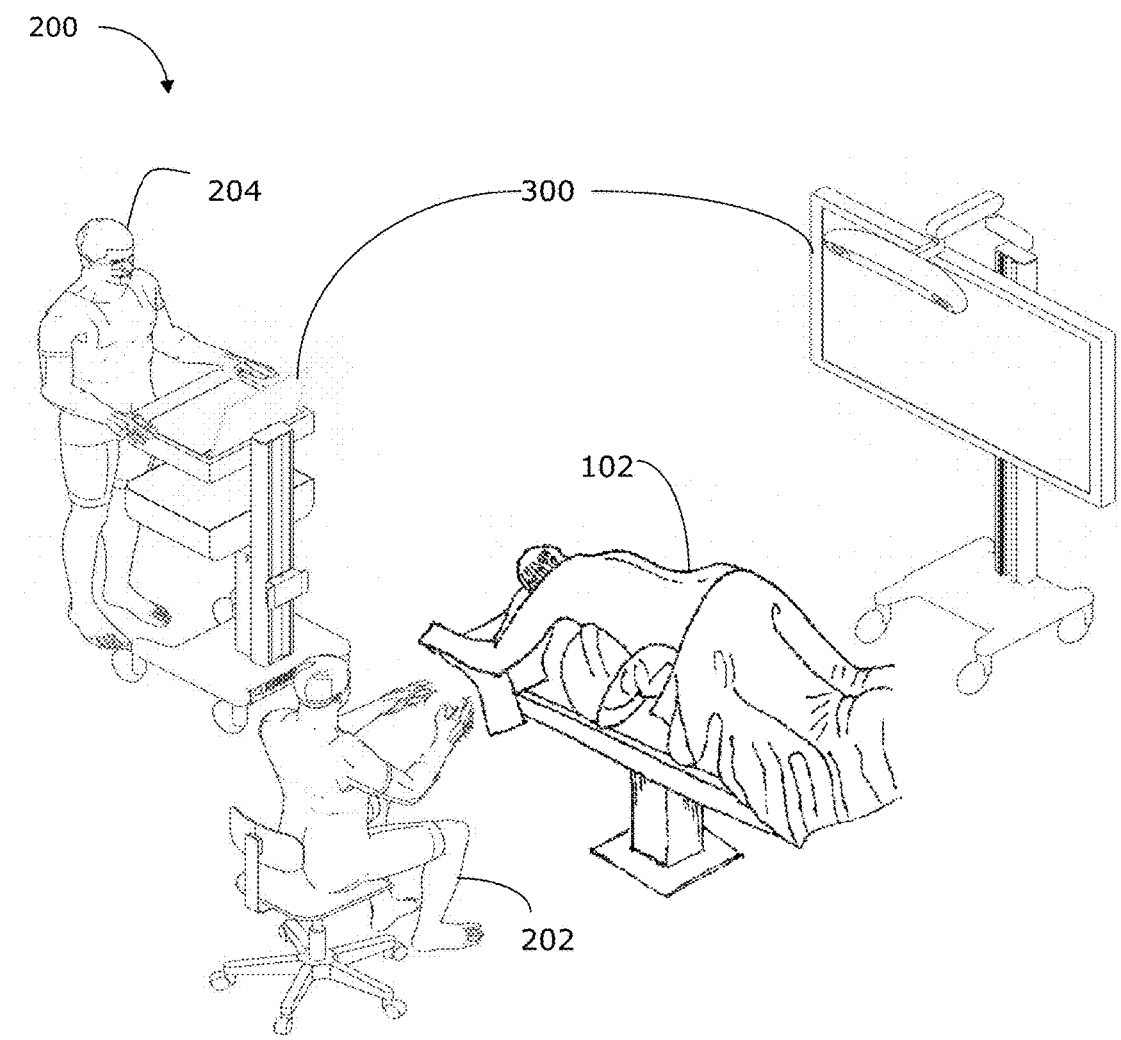
FIG. 2 shows an example operating room setup for an image guided spinal surgical procedure.

In FIG. 2, an operating room (OR) environment 200 is shown, which may be used to support navigated image-guided surgery. As shown in FIG. 2, a surgeon 202 conducts a medical procedure, for example a spinal procedure, on the patient 102 in the OR environment 200. A medical navigation system 300 (described further below) may include an equipment tower, tracking system and display(s) to provide image guidance and/or tracking information, to assist the surgeon 202 during the procedure. An operator 204 may also be present to operate and control the medical navigation system 300, as well as provide other assistance during the medical procedure.

Figure 3:
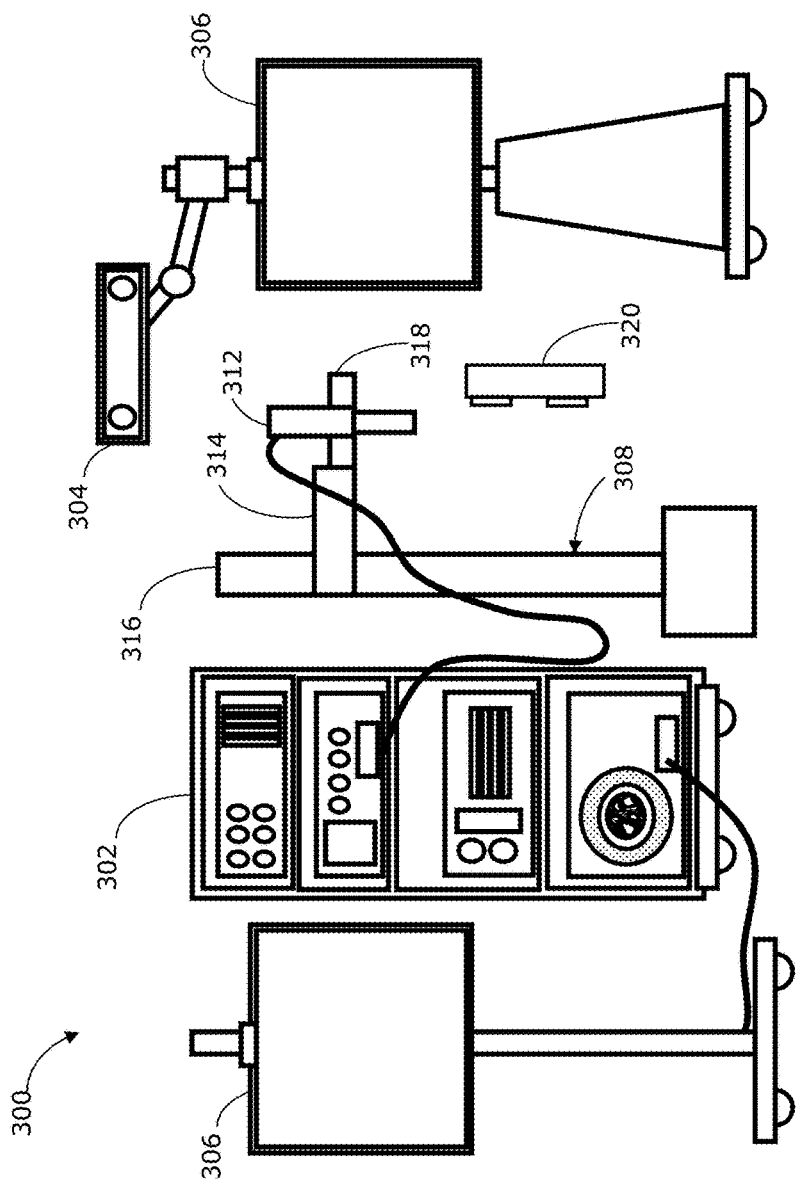
FIG. 3 shows an example navigation system suitable for image guided medical procedures.

FIG. 3 is a diagram illustrating example components of the navigation system 300. The navigation system 300 may provide intraoperative navigation assistance for various medical procedures, including spinal procedures or neural procedures. In the example shown, the navigation system 300 includes an equipment tower 302, a tracking system 304, one or more displays 306, and a positioning system 308. Although described as part of the navigation system 300, in some examples one or more components described with reference to and shown in FIG. 3 may be separate from the navigation system 300 (e.g., the tracking system 304 may be a separate system that operates in conjunction with the navigation system 300). The tracking system 304 may include an optical tracking device, tracking camera, video camera, infrared camera, or any other suitable camera or scanner based system. The tracking system 304 may be used to track markers (described further below) to obtain tracking data, which may be used to determine the position and orientation of a tracked object.

The positioning system 308 in this example includes an automated mechanical arm 314 (also referred to as a robotic arm or automated arm 314), a lifting column 316 and an end effector 318. The lifting column 316 is connected to a frame of the positioning system 308. In the example of FIG. 3, the proximal end of the automated arm 314 is connected to the lifting column 316. In other examples, the automated arm 314 may be connected to a horizontal beam, which is then either connected to the lifting column 316 or directly to the frame of the positioning system 308. The automated arm 314 may have multiple joints, for example to enable five, six or seven degrees of freedom.

The end effector 318 is attached to the distal end of the automated arm 314. The end effector 318 may accommodate a plurality of instruments or tools for the medical procedure. In FIG. 3, the end effector 318 is shown as holding an intraoperative imaging system 312 such as an optical scope and two-dimensional (2D) camera, however it should be noted that any alternate devices may be used with the end effector 318 including a wide field camera, microscope and Optical Coherence Tomography (OCT), video camera, or other imaging instruments, as well as devices other than an imaging system 312. In some examples, the intraoperative imaging system 312 may include a wide field camera in connection with an external scope, which may be held together by a single end effector 318. In another example, multiple end effectors 318 may be attached to the distal end of the automated arm 314, for example to hold different imaging systems to enable switching among multiple imaging modalities. In some examples, different end effectors 318 may provide different ranges of control (e.g., a microcontrol effector may be used to hold a laser-based ablation system).

The positioning system 308 may receive input information about the spatial position and orientation of the automated arm 314, end effector 318 and/or imaging system 312, and any tracked object. The position and orientation of the tracked object may be determined by the tracking system 304 by detection of one or more markers on the object. The position and orientation of the automated arm 314, end effector 318 and/or imaging system 312 may be determined by the tracking system 304 by detection of markers provided on the automated arm 314, end effector 318 and/or imaging system 312. In some examples, position sensors on the automated arm 314 may provide information about the position and orientation of the automated arm 314, and the position and orientation of the end effector 318 and/or imaging system 312 may be determined based on the known position and orientation of the end effector 318 and/or imaging system 312 relative to the automated arm 314.

The positioning system 308 may work in conjunction with the tracking system 304 to position the intraoperative imaging system 312 to maintain alignment with an object of interest, such as aligned with the passage of a retractor tube. For example, the positioning system 308 may compute the desired joint positions for the automated arm 314 so as to manoeuvre the end effector 318 to a predetermined spatial position and orientation relative to the tracked object. This predetermined relative spatial position and orientation may be designated as the "Zero Position", such as where the field-of-view (FOV) of the imaging device 312 is aligned with the tracked object.

Further, the positioning system 308, the tracking system 304 and the automated arm 314 may form a feedback loop. This feedback loop may work to keep the tracked object in constant view and focus of the imaging device 312 (e.g., where the end effector 318 holds the imaging device 312), as the tracked object may move during the procedure. The positioning system 308 may also include an input mechanism, such as a foot pedal, which may be activated to control the automated arm 314 to automatically align the imaging device 312 (e.g., held by the end effector 318) with the tracked object.

A handheld three-dimensional (3D) scanner 320 may be used to capture intraoperative 3D image data about the object of interest. The 3D scanner 320 may be used to capture a full or nearly full array scan of a patient's surface. This 3D image data may be provided as a 3D point cloud.

The image data captured by the intraoperative imaging system 312 may be displayed on one or more of the display(s) 306. The display(s) 306 may also display other image data, such as preoperative image data (e.g., MR or CT image data) or 3D image data, as well as other navigation information.

Figure 4:
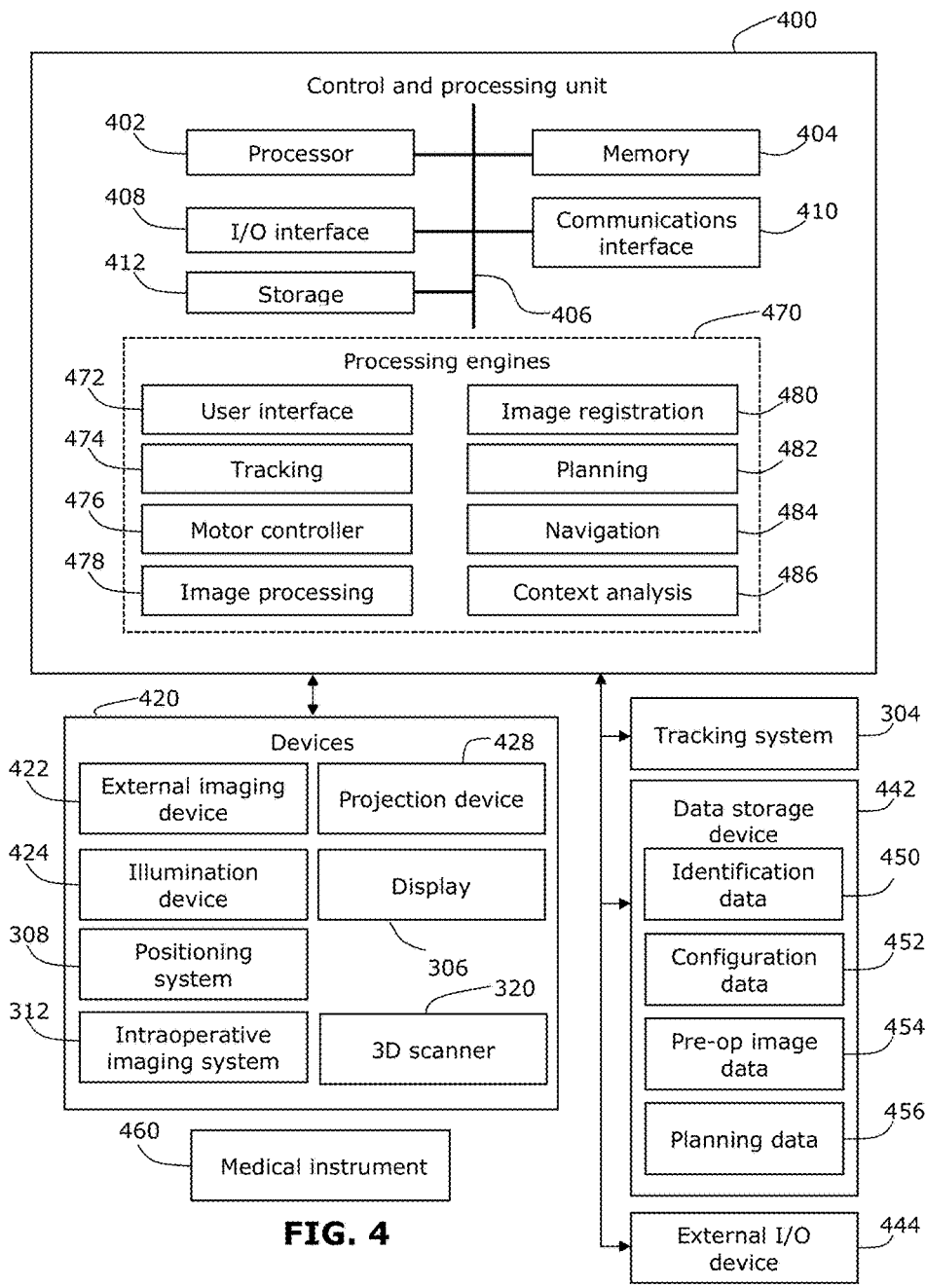
FIG. 4 is a block diagram illustrating an example control and processing system that may be used in the navigation system of FIG. 3.

In FIG. 4, a block diagram is shown illustrating a control and processing unit 400 that may be used in the medical navigation system 300 (e.g., as part of the equipment tower 302). Although FIG. 4 shows and is described with reference to a single instance of each component, in some examples there may be multiple instances of certain components.

As shown in FIG. 4, in an example, the control and processing system 400 may include a processor 402, a memory 404, a system bus 406, an input/output interface 408, a communications interface 410, and a storage device 412. The control and processing system 400 may be interfaced with other external devices/systems, such as the tracking system 304, a data storage device 442, and an external input and output device 444, which may include, for example, one or more of a display, keyboard, mouse, sensors attached to medical equipment, foot pedal, microphone or speaker. The data storage device 442 may be any suitable data storage device, such as a local or remote computing device (e.g. a computer, hard drive, digital media device, or server) having a database stored thereon.

In the example shown in FIG. 4, the data storage device 442 includes identification data 450 for identifying one or more medical instruments 460 and configuration data 452 that may associate configuration parameters with one or more of the medical instrument(s) 460. The data storage device 442 may also include preoperative image data 454 and/or medical procedure planning data 456. Although the data storage device 442 is shown as a single device in FIG. 4, in some examples the data storage device 442 may be provided as multiple storage devices.

The medical instrument 460 may be identifiable by the control and processing unit 400. The medical instrument 460 may be connected to and controlled by the control and processing unit 400, or the medical instrument 460 may be operated or otherwise employed independent of the control and processing unit 400. The tracking system 304 may be employed to track one or more of the medical instrument(s) 460. For example, one or more tracking markers may be provided on the medical instrument 460, or the medical instrument 460 may be coupled to a tracked object (e.g., a trackable sheath or a trackable frame).

The control and processing unit 400 may also interface with one or more devices 420, which may include configurable devices. The control and processing unit 400 may intraoperatively reconfigure one or more of such devices 420 based on configuration parameters obtained from the configuration data 452. Example devices 420 include an external imaging device 422, an illumination device 424, the positioning system 308, the intraoperative imaging system 312, a projection device 428, the display 306, and the 3D scanner 320.

The control and processing unit 400 may implement examples described herein, via the processor 402 and/or memory 404. For example, the functionalities described herein can be implemented via hardware logic in the processor 402 and/or using instructions stored in the memory 404, as one or more processing modules or engines 470. Example processing engines 470 include, but are not limited to, a user interface engine 472, a tracking engine 474, a motor controller 476, an image processing engine 478, an image registration engine 480, a procedure planning engine 482, a navigation engine 484, and a context analysis engine 486. While the example processing engines 470 are shown separately in FIG. 4, in some examples the processing engines 470 may be collectively stored as one or more sets of computer-readable instructions (e.g., stored in the memory 404). In some examples, two or more processing engines 470 may be used together to perform a function.

It is to be understood that the system is not intended to be limited to the components shown in FIG. 4. One or more components of the control and processing system 400 may be provided as an external component or device. For example, the navigation module 484 may be provided by an external navigation system that is integrated with the control and processing system 400

In some examples, the navigation system 300, which may include the control and processing unit 400, may provide tools to the surgeon that may help to improve the performance of the medical procedure and/or post-operative outcomes. In addition to spinal procedures, the navigation system 300 can also be used in the context of an orthopaedic procedure or a neural procedure, as well as medical procedures on other parts of the body such as breast biopsies, liver biopsies, and others. While some examples are described herein, examples of the present disclosure may be applied to any suitable medical procedure.

In some examples, a depth map may be generated to capture depth information about the site of interest. A depth map may be generated in various ways. Some examples are described in PCT Application No. PCT/CA2015/050651, and in PCT Application No. PCT/CA2016/050189, both incorporated herein by reference in their entirety. The depth information may include information about the varying depth on a surface of a surgical site.

The depth information may be obtained using any suitable depth detector. The depth information may also be obtained using a general imaging device that is not specifically designed to capture depth information. For example, depth information may be determined based on the depth of field (DOF) (also referred to as focus range) of the imaging device 312. The DOF may be defined as the distance between the nearest and farthest elements in the FOV of the imaging device 312 that appear in focus in a captured image. In some examples, the DOF and the midpoint between the "near" and "far" edges (e.g., the working distance) are controlled by the optics of the scope system, such as the imaging device 312, and by determining what sections of an image are in focus, where the distance or depth of those sections from the scope can be extracted or calculated. The control and processing unit 400 may control the imaging device 312 to change the working distance and capture images at different working distances. The control and processing unit 400 may then analyze the change in image focus over the different images and thus calculate depth information for different portions of the image. In this way, a depth map may be generated, which maps out depth information over the entire image. Narrowing the DOF may be used to increase the resolution in depth data.

In some examples, the 3D scanner 320 may instead be used to capture data about a 3D surface. The 3D scanner 320 may provide depth information directly to the control and processing unit 400 (e.g., without requiring further calculations to obtain depth information).

Depth information may be acquired over a site of interest, such as human tissue, for example a portion of a patient that is the subject of a medical procedure, for example vertebral bone and soft tissues around the spine. Generally, depth information may be obtained for each pixel in an image captured by the imaging device 312. This may be equally the case whether the captured image is static or a video image. The depth information may be used to generate a 3D point cloud and/or a 3D surface contour, for example.

Generally, the intraoperative image data obtained by the intraoperative imaging device 312 is in a coordinate space different from and independent of the coordinate space of the preoperative image data. More generally, different sets of image data may be in different coordinate spaces, even where the image data are all obtained intraoperatively or all obtained preoperatively, and even where the image data are obtained using the same imaging modality.

As well, tracking data obtained by the tracking system 304 is in a coordinate space different from and independent of the image coordinate spaces. Co-registration of these different sets of data may be achieved by performing a transformation mapping to map the sets of data into a common coordinate space. This may enable the sets of image data and tracking data to be presented together to provide navigation assistance to the surgeon during the medical procedure.

In some examples, the transformation mapping may be used to co-register two or more sets of intraoperative image data. For example, intraoperative MR or CT image data may be co-registered with intraoperative optical image data. In some examples, two or more sets of preoperative image data may be co-registered, for example co-registration of MR and CT image data. In some examples, the transformation mapping may be used to co-register two or more sets of image data obtained using the same imaging modality (e.g., between two sets of optical image data, or two sets of intraoperative CT image data). The image data may be further co-registered with the tracking data in a common coordinate space.

The common coordinate space may result from co-registration of one or more actual coordinate spaces and/or one or more virtual coordinate spaces. An actual coordinate space contains actual objects that exist in physical space and a virtual coordinate space contains virtual objects that are computer-generated in a virtual space.

Figure 5:
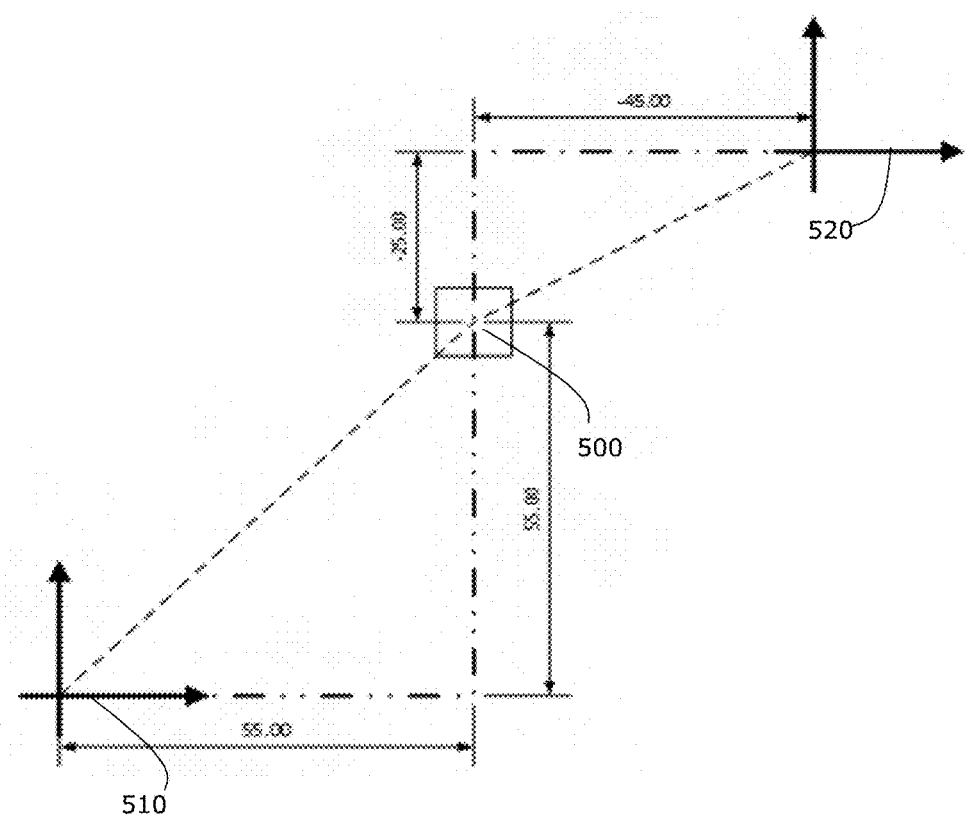
FIG. 5 is a diagram illustrating co-registration of two coordinate spaces.

FIG. 5 illustrates a simplified example of how two coordinate spaces may be co-registered by performing a transformation mapping, based on a common reference coordinate. In the example shown, a common reference coordinate 500 has a defined position and orientation in first and second coordinate spaces 510, 520. In the context of a medical procedure, the common reference coordinate 500 may be a fiducial marker or anatomical reference. The example depth-encoded marker described herein may serve as the common reference coordinate 500. For simplicity, although FIG. 5 illustrates co-registration of 2D coordinate spaces, co-registration may be performed for 3D coordinate spaces, including a depth dimension.

The position and orientation of the common reference coordinate 500 is used to correlate the position of any point in the first coordinate space 510 to the second coordinate space 520, and vice versa. The correlation is determined by equating the locations of the common reference coordinate 500 in both spaces 510, 520 and solving for a transformation variable for each degree of freedom defined in the two coordinate spaces 510, 520. These transformation variables may then be used to transform a coordinate element of a position in the first coordinate space 510 to an equivalent coordinate element of a position in the second coordinate space 520, and vice versa.

In FIG. 5, the common reference coordinate 500 has a coordinate position (x1, y1) determined in the first coordinate space 510 and a coordinate position (x2, y2) in the second coordinate space 520. In the example shown, (x1, y1)=(55, 55) and (x2, y2)=(−45, −25).

Utilizing transformation equations, any point in the first coordinate space 510 may be related to the second coordinate space 520 via translation variables (xT, yT), as shown below:

$$x1=x2+xT$$

$$y1=y2+yT$$

Using the coordinate positions of the common reference coordinate 500, the transformation variables may be solved as follows:

$$55=-45+yT$$

$$100=yT$$

$$55=-25+xT$$

$$80=xT$$

The transformation variables may then be used to transform any coordinate point in the first coordinate space 510 to the second coordinate space 520, and vice versa, thereby co-registering the coordinate spaces 510, 520. For transformation between 3D coordinate spaces, similar calculations may be performed for position (x, y, z-coordinates) as well as for orientation (pitch, yaw, roll). In general, a transformation mapping may be performed to register two or more coordinate spaces with each other. Where there are more than two coordinate spaces to be co-registered, the transformation mapping may include multiple mapping steps.

As described above, using the handheld 3D scanner 320, a full or nearly full array scan of a surface of interest can be achieved intraoperatively. This may provide an order of magnitude greater point information than the surface tracking methods used in conventional approaches. The intraoperative image data obtained by the 3D scanner 320 may be provided as a 3D point cloud, in an intraoperative image coordinate space. This point cloud may be mapped to a surface in preoperative image data (e.g., MR or CT volumetric scan data), using a reference marker that is imageable by both preoperative and intraoperative imaging systems. The tracking system 304 may have no reference to the 3D point cloud data. Therefore, a transformation mapping between the tracking coordinate space and the intraoperative image coordinate space may be used so that tracking data can also be registered to the preoperative and intraoperative image data.

The present disclosure describes a marker to enable co-registration of two or more sets of image data (e.g., intraoperative image data and preoperative image data) and tracking data. To facilitate more accurate and faster registration of 3D coordinate spaces, the marker includes depth-encoded information, such that the position and orientation of the marker in 3D space may be more accurately and/or quickly determined in the image data. In particular, the marker has an asymmetry in a depth dimension, where the asymmetry is detectable in the two or more sets of image data (e.g., detectable in both intraoperative and preoperative imaging modalities).

Figure 6A:
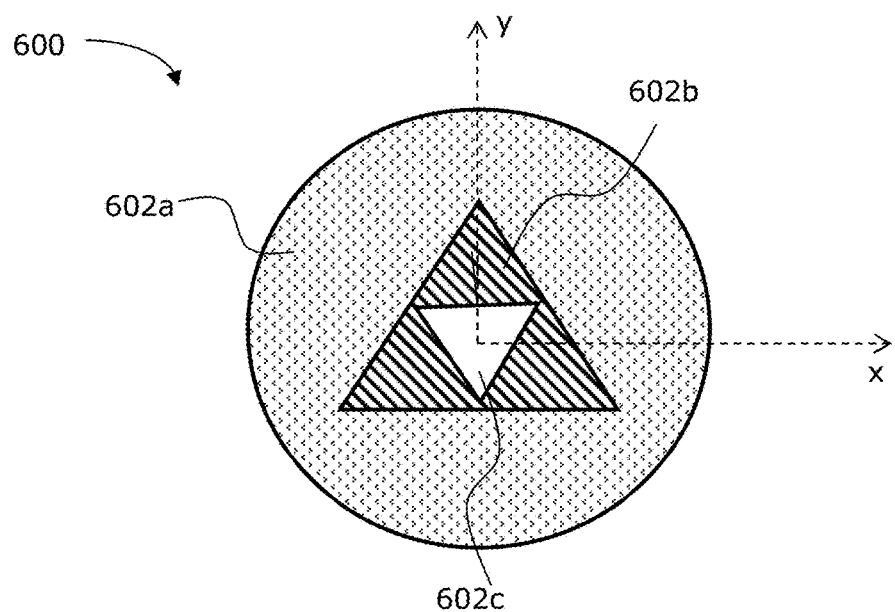
FIGS. 6A-6C illustrate example depth-encoded markers that may be used for image registration in image guided medical procedures.
Figure 6B:
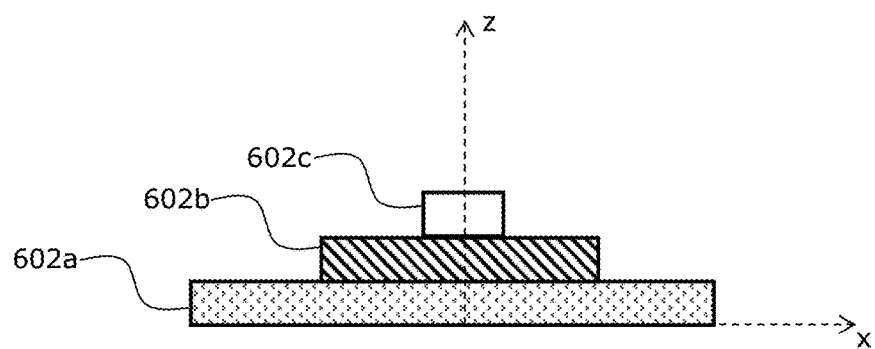

FIGS. 6A and 6B show an example depth-encoded fiducial marker 600 that may be used for intraoperative image registration. For ease of reference, x, y and z-axes are represented in FIGS. 6A and 6B; these axes are shown as an example only, are defined with respect to the example marker 600, and are not necessarily the same as the coordinate axes in the image data or tracking data. FIG. 6A shows the example marker 600 looking down on the x-y plane, while FIG. 6B shows the example marker 600 looking down on the x-z plane. By "depth-encoded", it is meant that the marker 600 has detectable variations along the depth dimension. In particular, the marker 600 may include two or more features that provide the marker 600 with asymmetry in at least the depth dimension, where the asymmetry is detectable by the imaging systems of interest. For example, such asymmetry may be detectable by at least preoperative and intraoperative imaging systems, or by two intraoperative imaging systems. Asymmetry in the depth dimension means that, in the image data sets of interest, the image of the marker 600 is non-uniform and not symmetrical along the depth axis (such that it can be uniquely determined directly from the image data whether the marker 600 is facing upwards or flipped downwards). The depth axis of the marker 600 may also be referred to as the z-axis, and the depth dimension may also be referred to as the z-dimension.

In some examples, the marker 600 is affixable on the x-y plane to the object of interest, for example using an adhesive. The marker 600 may also be simply placed on the object of interest without being affixed, for example where the object of interest is expected to be stationary at least for the duration of image capture. The x- and y-dimensions of the marker 600 may be greater than the z-dimension. As noted above, the asymmetry of the marker 600 in the depth dimension enables the z-orientation of the marker 600 to be uniquely determined. In conventional markers that do not have asymmetry in depth, the orientation of the marker cannot be uniquely determined from an image of the marker taken in the x-z plane or y-z plane—the image of the conventional marker appears the same whether the marker is facing upwards or flipped downwards.

In the example shown in FIGS. 6A and 6B, the asymmetry of the marker 600 includes overlapping layers 602a, 602b, 602c that have different dimensions, geometries and/or orientations. The different overlapping layers 602a, 602b, 602c may give rise to differences in image intensities when captured in certain imaging modalities (e.g., a single layer 602a may have lower image intensity than two overlapped layers 602a, 602b, in MR image data). The overlapping layers 602a, 602b, 602c may also have a non-negligible thickness (e.g., having a thickness of 2 mm or greater), resulting in a 3D geometry (as more clearly shown in FIG. 6B) that has detectable changes in dimension along the depth dimension of the marker 600. Each of the overlapping layers 602a, 602b, 602c may also be provided with different textures and/or may be made of materials with different densities (which may give rise to detectable differences in image intensities).

Figure 6C:
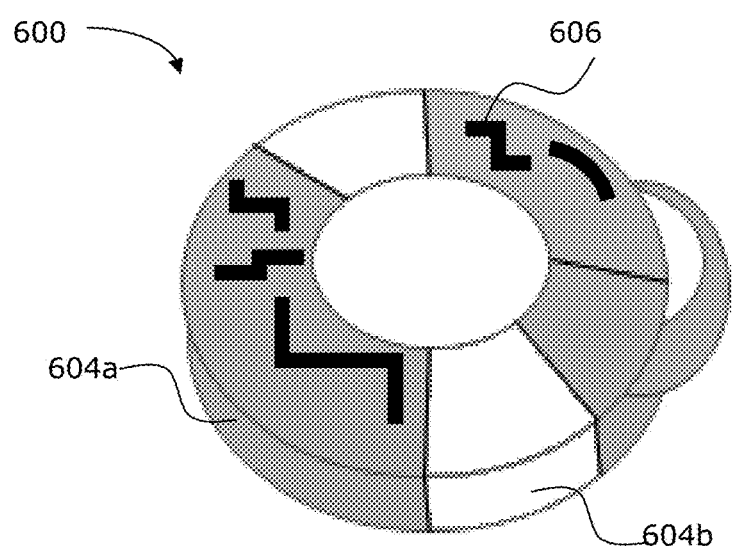

In the example shown in FIG. 6C, the depth-encoded marker 600 includes multiple compartments 604a, 604b containing materials that give rise to different imaging intensities in at least one of the image data sets. For example, the compartments 604a may contain air while the compartments 604b may contain a liquid (e.g., water) or gel. The different materials contained in the compartments 604a, 604b give rise to hypo or hyper intensity in the image data set (e.g., CT or MR image) that may help to increase the speed and/or accuracy of image processing to determine the 3D location of the marker 600 in the image data set.

The marker 600 shown in FIG. 6C further includes one or more 2D objects 606. The 2D objects 606 may have unique geometries, orientations and/or colours that are known or calibrated beforehand. Such 2D objects 606 may be uniquely detectable in at least one of the image data sets. For example, the 2D objects 606 may enable a determination of the orientation of the marker 600 in image data captured by a 2D optical imaging system.

Generally, the asymmetry of the marker 600 may arise from two or more asymmetrical features on the marker 600 having detectable differences which may be optical differences (e.g., different textures, colours, edges or patterns).

In some examples, the marker 600 may also serve as a tracking marker that is trackable by a tracking system (e.g., the tracking system 304 described above).

The marker 600 may be placed on any object of interest. The marker 600 may be provided on any rigid object, for example, including hard tissues such as bone (e.g., spinal vertebrae, skull, intact bone or bone fragments) as well as other objects in the surgical field such as medical instruments or tools (e.g., retractors, tubes, clamps or pins). For example, the marker 600 may be attached to a surgical instrument or implant, or may be fixed to another object (e.g., surgical table) within the FOV of the imaging systems. In some examples, the marker 600 may be integrated with the surgical instrument or implant, or other object, rather than a separate component attached to the surgical instrument or implant, or other object. For example, the marker 600 may be part of a surgical instrument (e.g., a specific region of the surgical instrument) or otherwise permanently attached to the instrument. The marker 600 may be placed or affixed directly to an anatomical object of interest. Generally, a single marker 600 may be sufficient for each object of interest. Because the marker 600 is depth-encoded, the position and orientation of the object of interest associated with the marker 600 may be determined without using multiple markers (as is typically the case for conventional markers without depth-encoding), thus requiring a smaller footprint. Where there are multiple objects of interest, multiple markers 600 may be used, each object of interest being provided with a respective one marker 600. In some examples, where there are multiple markers 600 being captured in the same FOV, the markers 600 may be unique (e.g., having different 2D objects 606 and/or different geometries) to facilitate quicker and/or more accurate identification of each marker 600.

Figure 7A:
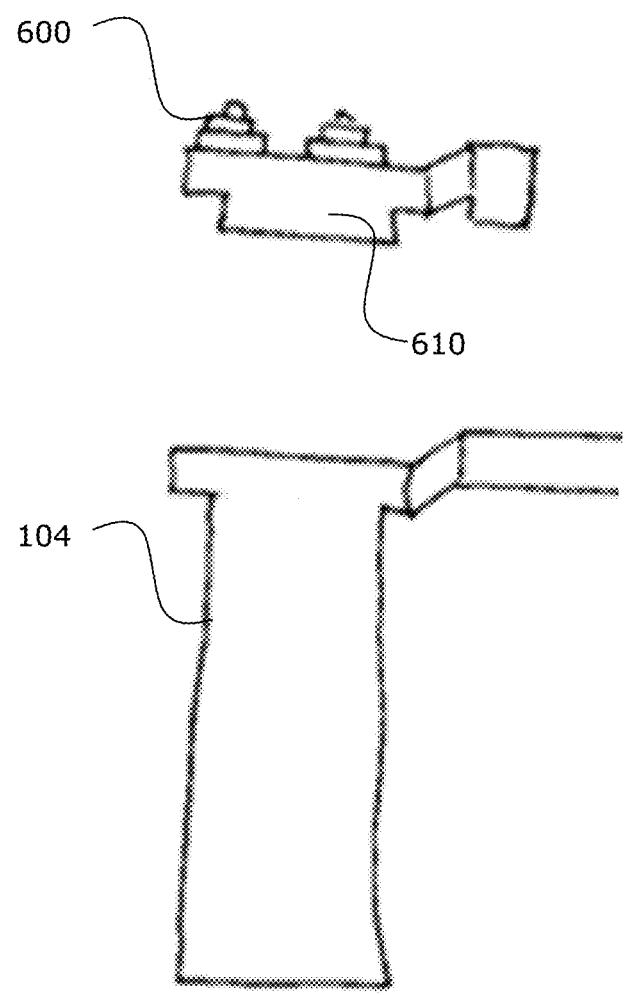
FIGS. 7A-7C illustrate example placements of the depth-encoded markers of FIGS. 6A-6C.

FIG. 7A shows an example marker 600 that is removably attachable to the retractor tube 104. For example, one or more markers 600 may be provided on a base 610 that is removably attachable (e.g., snapped onto) the proximal end of the retractor tube 104.

Figure 7B:
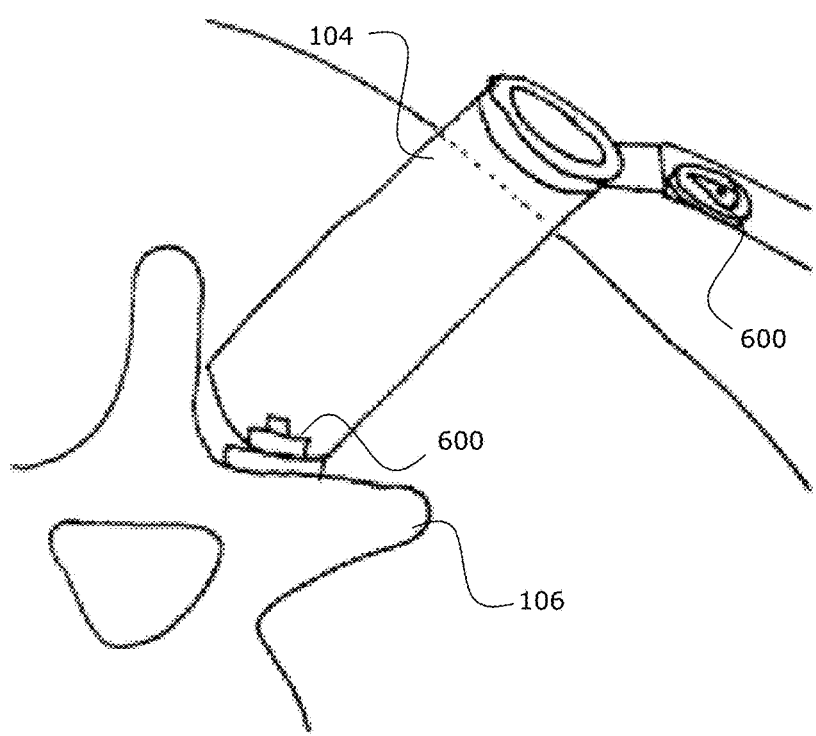

In FIG. 7B, the example marker 600 may be removably attachable (e.g., using an adhesive or other surgical fastener such as surgical pins or surgical screws) directly to the retractor tube 104 and/or to the spine 106. The marker 600 may be placed on the spine 106, instead of affixing the marker 600 to the spine 106.

Figure 7C:
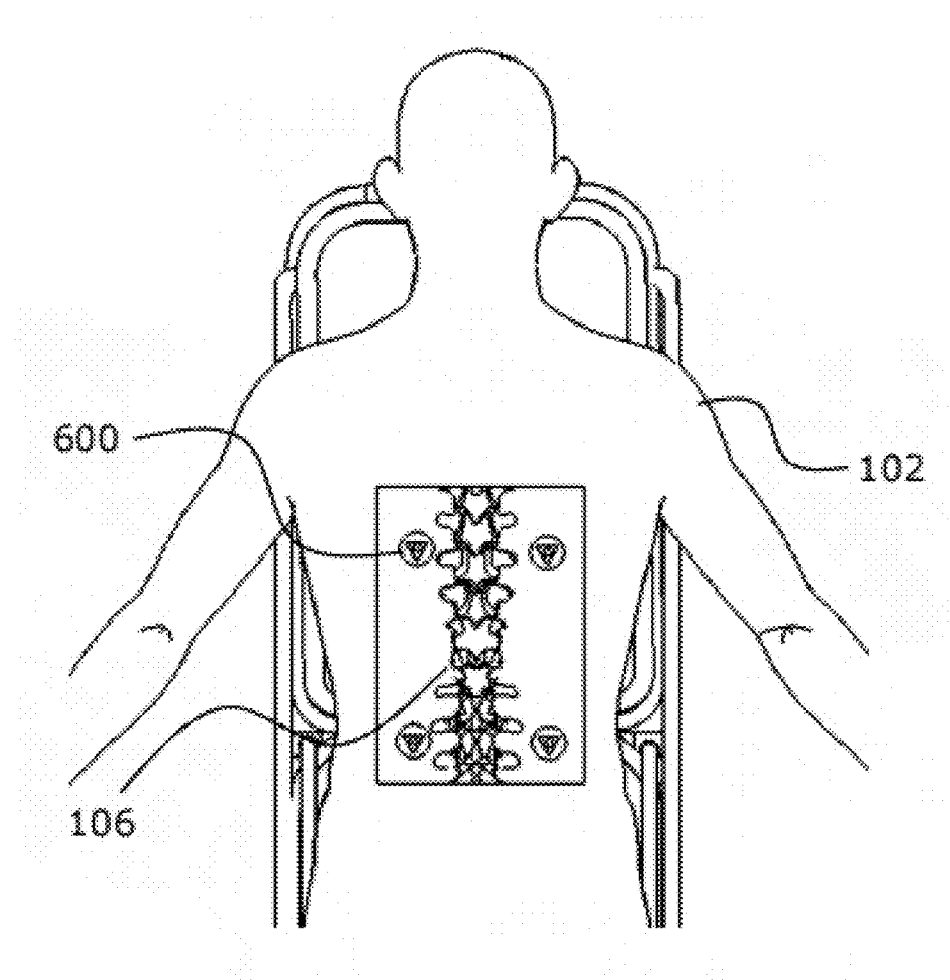

In FIG. 7C, the example marker 600 may be removably attachable to the skin surface of the patient 102, in the vicinity of the surgical site.

In some examples, the marker 600 may be provided on a frame (not shown), which may be affixed to the object of interest. The frame may also hold other reference markers, such as a tracking marker. The frame may have other features, such as a known 3D geometry, to help increase accuracy during image registration.

Figure 8:
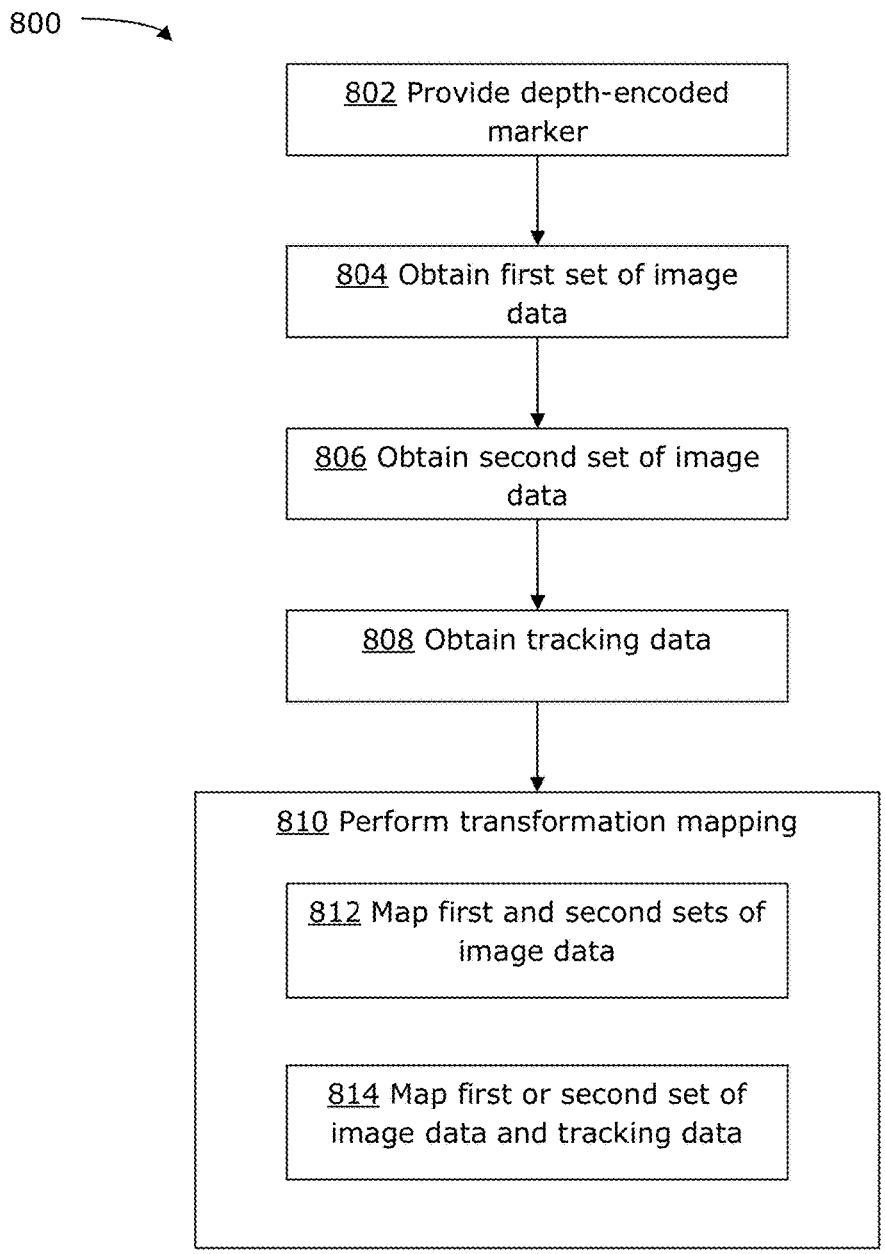
FIG. 8 is a flowchart illustrating an example method for image registration using a depth-encoded marker.

FIG. 8 is a flowchart illustrating an example method 800 for image registration using a depth-encoded marker. The method 800 may be implemented using the navigation system 300 described above. For example, one or more steps described below may be performed by the control and processing unit 400 of the navigation system 300 (e.g., by the processor 402), and instructions for one or more steps of the method 800 may be stored in the memory 404 of the control and processing unit 400.

At 802, a depth-encoded marker, such as the example markers 600 described above, is provided on an object of interest. The marker may be affixed to the object of interest (e.g., using an adhesive) or may be placed without affixing. The object of interest may be a medical instrument, an anatomical feature or other object within the FOV of the imaging systems. For example, the marker may be provided on any suitable object, including hard tissues such as bone (e.g., spinal vertebrae, skull, intact bone or bone fragments). The marker may also be provided on or integrated with other objects in the surgical field such as medical instruments or tools (e.g., retractors, tubes, clamps or pins) or the surgical bed. In some examples, a plurality of markers may be used, for example one marker being provided on a respective one of a plurality of objects of interest.

At 804, a first set of image data is obtained. The first set of image data may be preoperative image data, for example obtained using CT or MR imaging (including diffusion-weighted MR or diffusion tensor imaging). The first set of image data includes the object(s) of interest and also encompasses the marker(s). Where the image data is preoperative image data, the image data may be stored in a memory of the navigation system, for example, and obtaining the image data may include retrieving the image data from memory.

At 806, a second set of image data is obtained. The second set of image data may be intraoperative image data, for example obtained using a 3D scanner or a 2D optical camera. The second set of image data also includes the object(s) of interest and also encompasses the marker(s).

In some examples, the first and second sets of image data may be both intraoperative image data or may be both preoperative image data. The first and second sets of image data may be obtained using different imaging modalities, or using the same imaging modality. The first and second sets of image data may be in different independent image coordinate spaces.

At 808, tracking data is obtained, to track the depth-encoded marker or other tracking marker intraoperatively. For example, the depth-encoded marker may itself be trackable. In examples where tracking marker(s) are provided separately from the depth-encoded marker(s), the tracking marker(s) may be provided on the same or different objects of interest. The tracking data may be obtained by a tracking system, such as the tracking system 304 described above. The tracking data may be in a tracking coordinate space that is different and independent from the first and second image coordinate spaces.

At 810, a transformation mapping is performed to register the first set of image data, the second set of image data and the tracking data to each other. The result of the transformation mapping may be a common coordinate space.

The transformation mapping may involve, at 812, mapping the first and second sets of image data to each other. This mapping may be based on the 3D position and orientation of the depth-encoded marker in each of the first and second sets of image data. For example, appropriate image processing techniques may be used to process each set of image data in order to detect the position and orientation of the marker. The asymmetry of the marker, as described above, may enable the orientation of the marker to be unambiguously determined. The asymmetry of the marker may also facilitate faster and more accurate detection of the marker in the first and/or second sets of image data.

The transformation mapping may also involve, at 814, mapping the first or second set of image data and the tracking data to each other. This mapping may be based on the 3D position and orientation of the depth-encoded marker, or may be based on a different marker such as a tracking marker. For example, the depth-encoded marker may include features (e.g., optically-detectable patterns) to enable detection by the tracking system. In other examples, the depth-encoded marker may not be detectable by the tracking system, but the tracking marker may have a feature (e.g., 3D geometry) that is detectable in the first or second set of image data.

While the depth-encoded marker is detectable in both the first and second sets of image data, a tracking marker may be detectable in only one set of image data. For example, the tracking marker may not be present when preoperative image data is obtained and may be present only when intraoperative image data is obtained. Where the depth-encoded marker also functions as a tracking marker, the depth-encoded marker may be present and detectable in all of the first and second sets of image data and the tracking data.

The mappings 812, 814 performed as part of transformation mapping 810 may take place in parallel or in series, and may occur in any order. The mappings 812, 814 may be performed independently of each other. For example, the mapping of intraoperative image data to tracking data may be performed more frequently to account for the dynamic nature of the tracking data, compared to the static preoperative image data. Both mappings 812, 814 may be performed based on the same marker (e.g., both performed using the depth-encoded marker as the common reference coordinate) or based on different markers (e.g., performing one mapping 812 using the depth-encoded marker as the common reference coordinate and the other mapping 814 using a tracking marker as the common reference coordinate).

The result of the transformation mapping 810 is a set of registration data, which represents the transformation to correlate between the first set of image data, second set of image data and tracking data. For example, the registration data may be stored as one or more transformation matrices.

Generally, although obtaining preoperative image data at 804 may not be repeatedly performed, obtaining intraoperative image data at 806 and obtaining tracking data at 808 may be repeated throughout the medical procedure.

The transformation mapping at 810 may be repeatedly updated throughout the medical procedure, for example as the FOV of intraoperative image data changes. In some examples, only a portion of the transformation mapping 810 may be updated, such as the mapping 814 of intraoperative image data with tracking data, which may be updated in situations where one or more tracking markers move in or out of the FOV of the tracking system.

In some examples, an additional depth-encoded marker may be provided during the procedure, for example where a previously placed depth-encoded marker becomes obscured. The transformation mapping 810 may be updated intraoperatively to reflect this additional depth-encoded marker. For example, mapping 812 between preoperative and intraoperative image data may be unchanged, but mapping 814 between intraoperative image data and tracking data may be updated.

The registration data may be provided to a navigation system (e.g., the navigation system 300 described above), to provide navigation assistance to a surgeon. For example, using the co-registered tracking data and image data sets, a visual display may be provided where a virtual representation of a tracked object is superimposed on a 3D rendering of the preoperative image data, which is also overlaid with depth information obtained from intraoperative image data. Other similar navigation assistance may be provided in situations where both first and second sets of image data are intraoperative image data, for example. The registration data may also be stored (e.g., in a memory of the navigation system), for example for future use or to be referenced by other systems. The registration information may be used in any application where co-registered image data may be appropriate (e.g., for output to a 2D or 3D display, output to an augmented reality display, or to provide navigational feedback to a surgeon).

Although the above discussion refers to the surgeon as being the user who controls and uses the examples of the present disclosure, it should be understood that the present disclosure is not limited to any specific user. In some examples, there may be a plurality of users involved.

While some embodiments or aspects of the present disclosure may be implemented in fully functioning computers and computer systems, other embodiments or aspects may be capable of being distributed as a computing product in a variety of forms and may be capable of being applied regardless of the particular type of machine or computer readable media used to actually effect the distribution.

At least some aspects disclosed may be embodied, at least in part, in software. That is, some disclosed techniques and methods may be carried out in a computer system or other data processing system in response to its processor, such as a microprocessor, executing sequences of instructions contained in a memory, such as read-only memory (ROM), volatile random access memory (RAM), non-volatile memory, cache or a remote storage device.

A computer readable storage medium may be used to store software and data which when executed by a data processing system causes the system to perform various methods or techniques of the present disclosure. The executable software and data may be stored in various places including for example ROM, volatile RAM, non-volatile memory and/or cache. Portions of this software and/or data may be stored in any one of these storage devices.

Examples of computer-readable storage media may include, but are not limited to, recordable and non-recordable type media such as volatile and non-volatile memory devices, ROM, RAM, flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Furthermore, at least some of the methods described herein may be capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

At least some of the elements of the systems described herein may be implemented by software, or a combination of software and hardware. Elements of the system that are implemented via software may be written in a high-level procedural language such as object oriented programming or a scripting language. Accordingly, the program code may be written in C, C++, J++, or any other suitable programming language and may comprise modules or classes, as is known to those skilled in object oriented programming. At least some of the elements of the system that are implemented via software may be written in assembly language, machine language or firmware as needed. In either case, the program code can be stored on storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

While the teachings described herein are in conjunction with various embodiments for illustrative purposes, it is not intended that the teachings be limited to such embodiments. On the contrary, the teachings described and illustrated herein encompass various alternatives, modifications, and equivalents, without departing from the described embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

The invention claimed is:

1. A method of performing intraoperative image registration during a medical procedure, the method comprising:
    providing a depth-encoded marker to an object of interest, the marker being imageable by at least two imaging systems, the marker having asymmetry in at least a depth dimension that is detectable by the at least two imaging systems;
    obtaining a first set of image data of the object of interest using a first imaging system, the first set of image data encompassing the marker, the first set of image data being in a first image coordinate space;
    obtaining a second set of image data of the object of interest using a second imaging system, the second set of image data encompassing the marker, the second set of image data being in a second image coordinate space;
    obtaining tracking data tracking the same or different marker, using a tracking system, the tracking data being in a tracking coordinate space;
    the first image coordinate space, the second image coordinate space and the tracking coordinate space being independent from each other;
    performing a transformation mapping to register the first set of image data, the second set of image data and the tracking data to each other by:
        mapping the first and second sets of image data to each other based on determination of three-dimensional (3D) position and orientation of the marker in each of the first and second sets of image data; and
        mapping the first or second set of image data and the tracking data to each other based on a determination of 3D position and orientation of the same or different marker in each of the tracking data and the first or second set of image data.

2. The method of claim 1, wherein the first imaging system is a magnetic resonance (MR) imaging system or a computed tomography (CT) imaging system.

3. The method of claim 1, wherein the second imaging system is a 3D scanner, and wherein the second set of image data comprises a 3D point cloud.

4. The method of claim 1, wherein the second imaging system is a two-dimensional (2D) optical imaging system.

5. The method of claim 1, wherein the asymmetry of the marker comprises two or more components having different densities.

6. The method of claim 1, wherein the asymmetry of the marker comprises two or more overlapping layers.

7. The method of claim 1, wherein the asymmetry of the marker comprises two or more different textures.

8. The method of claim 1, wherein the asymmetry of the marker comprises two or more compartments filled with materials having different imaging intensities when imaged by the first or second imaging system.

9. The method of claim 1, wherein the marker further comprises at least one two-dimensional (2D) object detectable by at least one of the first or second imaging system, the 2D object being configured to enable determination of orientation of the marker.

10. The method of claim 1, wherein the object of interest comprises a spinal surgical object.

11. The method of claim 1, wherein there is a plurality of objects of interest, each object of interest being provided with one respective marker.

12. The method of claim 1, wherein providing the depth-encoded marker to the object of interest comprises providing the depth-encoded marker integrated with the object of interest.

13. A system for performing intraoperative image registration during a medical procedure, the system comprising:
    a depth-encoded marker for an object of interest, the marker being imageable by at least two imaging systems, the marker having asymmetry in at least a depth dimension that is detectable by the at least two imaging systems;
    a tracking system for obtaining intraoperative tracking data of the same or different marker, the tracking data being in a tracking coordinate space;
    a navigation system in communication, the navigation system comprising a memory and a processor, the memory storing a first set of image data of the object of interest, the first set of image data encompassing the marker, the first set of image data being in a first image coordinate space; and
    an imaging system for obtaining a second set of image data of the object of interest, the second set of image data encompassing the marker, the second set of image data being in a second image coordinate space;
    the first image coordinate space, the second image coordinate space and the tracking coordinate space being independent from each other;
    wherein the processor of the navigation system is configured to:

receive the tracking data and the second set of image data from the tracking system and the imaging system, respectively;

perform a transformation mapping to register the first set of image data, the second set of image data and the tracking data to each other by:

mapping the first and second sets of image data to each other based on determination of three-dimensional (3D) position and orientation of the marker in each of the first and second sets of image data; and mapping the first or second set of image data and the tracking data to each other based on a determination of 3D position and orientation of the same or different marker in each of the tracking data and the first or second set of image data; and store registration data in the memory based on the transformation mapping.

14. The system of claim 13, wherein the first set of image data is magnetic resonance (MR) image data or computed tomography (CT) image data.

15. The system of claim 13, wherein the imaging system is a 3D scanner, and wherein the second set of image data comprises a 3D point cloud.

16. The system of claim 13, wherein the imaging system is a two-dimensional (2D) optical camera.

17. The system of claim 13, wherein the asymmetry of the marker comprises two or more components having different densities.

18. The system of claim 13, wherein the asymmetry of the marker comprises two or more overlapping layers.

19. The system of claim 13, wherein the asymmetry of the marker comprises two or more different textures.

20. The system of claim 13, wherein the asymmetry of the marker comprises two or more compartments filled with materials having different imaging intensities in at least one of the first or second set of image data.

21. The system of claim 13, wherein the marker further comprises at least one two-dimensional (2D) object detectable in at least one of the first or second set of image data, the 2D object being configured to enable determination of orientation of the marker.

22. The system of claim 13, wherein the object of interest comprises a spinal surgical object.

23. The system of claim 13, wherein there is a plurality of markers, each marker being for a respective object of interest.

24. The system of claim 13, wherein the depth-encoded marker is integrated with the object of interest.

* * * * *